(12) United States Patent
Guo

(10) Patent No.: US 10,610,293 B2
(45) Date of Patent: Apr. 7, 2020

(54) DEFLECTABLE CATHETER BODIES WITH CORRUGATED TUBULAR STRUCTURES

(71) Applicant: St. Jude Medical, Cardiology Division, Inc., St. Paul, MN (US)

(72) Inventor: Xiaoping Guo, Eden Prairie, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 412 days.

(21) Appl. No.: 15/106,155

(22) PCT Filed: Nov. 25, 2014

(86) PCT No.: PCT/US2014/067307
§ 371 (c)(1),
(2) Date: Jun. 17, 2016

(87) PCT Pub. No.: WO2015/099935
PCT Pub. Date: Jul. 2, 2015

(65) Prior Publication Data
US 2016/0317220 A1   Nov. 3, 2016

Related U.S. Application Data

(60) Provisional application No. 61/920,603, filed on Dec. 24, 2013.

(51) Int. Cl.
*A61B 18/14* (2006.01)
*A61M 25/00* (2006.01)
(Continued)

(52) U.S. Cl.
CPC ....... *A61B 18/1492* (2013.01); *A61M 25/005* (2013.01); *A61M 25/0009* (2013.01);
(Continued)

(58) Field of Classification Search
CPC .......... A61B 18/1492; A61B 2017/003; A61B 2017/00305; A61B 2017/00309;
(Continued)

(56) References Cited

U.S. PATENT DOCUMENTS 5,337,733 A * 8/1994 Bauerfeind ........ A61B 1/00071
600/114
5,520,222 A * 5/1996 Chikama .............. A61B 1/0055
138/103
(Continued)

FOREIGN PATENT DOCUMENTS

EP   1033107   9/2000
EP   2327365   6/2011
(Continued)

OTHER PUBLICATIONS

International Search Report and Written Opinion for PCT/US2013/039997, dated Oct. 16, 2013.
(Continued)

*Primary Examiner* — Jaymi E Della
(74) *Attorney, Agent, or Firm* — Wiley Rein LLP

(57) ABSTRACT

A guidable, or steerable, or deflectable catheter is provided that includes a proximal portion and a distal portion for insertion into a body cavity. A selectively deflectable segment having an anisotropic bending stiffness for deflection in individual planes is incorporated into the distal portion of the catheter shaft. The deflectable segment comprises a corrugate structure that provides smooth curvatures of desirable configurations, deflection planarity, and easiness.

20 Claims, 5 Drawing Sheets

(51) Int. Cl.
*A61M 25/01* (2006.01)
*B29C 65/02* (2006.01)
*A61B 18/00* (2006.01)
*B29K 77/00* (2006.01)
*B29L 31/00* (2006.01)

(52) U.S. Cl.
CPC .... *A61M 25/0045* (2013.01); *A61M 25/0147* (2013.01); *B29C 65/02* (2013.01); *A61B 2018/00351* (2013.01); *A61B 2018/00357* (2013.01); *B29K 2077/00* (2013.01); *B29L 2031/7542* (2013.01)

(58) Field of Classification Search
CPC ........... A61B 2017/00318; A61B 2017/00323; A61M 25/005; A61M 25/0045
See application file for complete search history.

(56) References Cited

U.S. PATENT DOCUMENTS

| | | | |
|---|---|---|---|
| 5,527,325 A * | 6/1996 | Conley | A61B 17/32078 604/525 |
| 6,440,120 B1 * | 8/2002 | Maahs | A61F 2/013 604/264 |
| 7,465,288 B2 | 12/2008 | Dudney et al. | |
| 7,985,215 B2 | 7/2011 | Guo et al. | |
| 8,016,784 B1 | 9/2011 | Hayzelden et al. | |
| 8,187,267 B2 | 5/2012 | Pappone et al. | |
| 8,374,670 B2 | 2/2013 | Selkee | |
| 2002/0165461 A1 | 11/2002 | Hayzelden et al. | |
| 2005/0070844 A1 | 3/2005 | Chow et al. | |
| 2007/0244550 A1 * | 10/2007 | Eidenschink | A61L 29/04 623/1.49 |
| 2007/0270679 A1 | 11/2007 | Nguyen et al. | |
| 2007/0299424 A1 * | 12/2007 | Cumming | A61M 25/0012 604/527 |
| 2009/0163915 A1 * | 6/2009 | Potter | A61B 18/1492 606/41 |
| 2009/0171348 A1 | 7/2009 | Guo et al. | |
| 2010/0152731 A1 | 6/2010 | de la Rama et al. | |
| 2010/0168717 A1 * | 7/2010 | Grasse | A61L 29/041 604/524 |
| 2012/0065633 A1 * | 3/2012 | Yagi | A61B 18/04 606/28 |

FOREIGN PATENT DOCUMENTS

| | | | | |
|---|---|---|---|---|
| EP | 2347726 | 7/2011 | | |
| JP | H07265432 | 10/1995 | | |
| JP | 2009/533174 | 9/2009 | | |
| JP | 2009/537244 | 10/2009 | | |
| JP | 2012/518470 | 8/2012 | | |
| WO | 98/29657 | 7/1998 | | |
| WO | 2007/121131 | 10/2007 | | |
| WO | 07/136981 | 11/2007 | | |
| WO | 09/097650 | 8/2009 | | |
| WO | 2010/096347 | 8/2010 | | |
| WO | WO2010113914 | * | 10/2010 | A61B 18/12 |
| WO | 11/132409 | 10/2011 | | |
| WO | 14/153275 | 9/2014 | | |

OTHER PUBLICATIONS

International Search Report and Written Opinion for PCT/US2014/067307, dated Mar. 23, 2015.

* cited by examiner

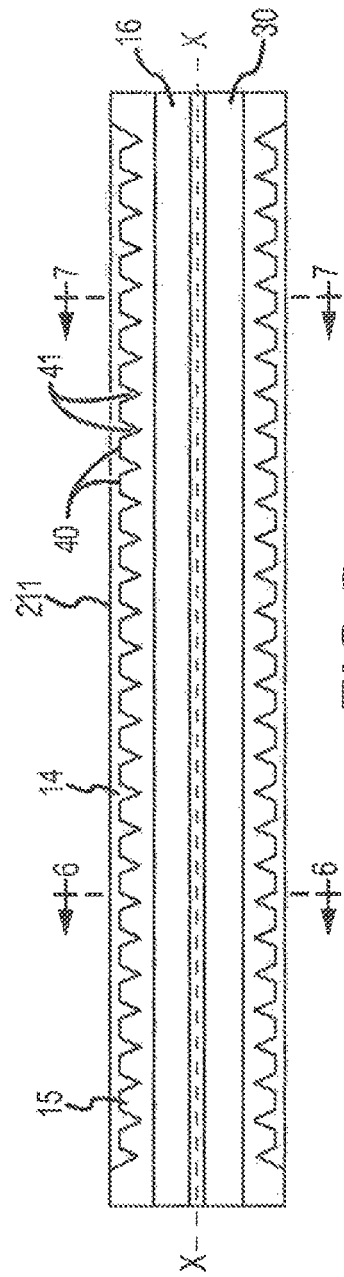
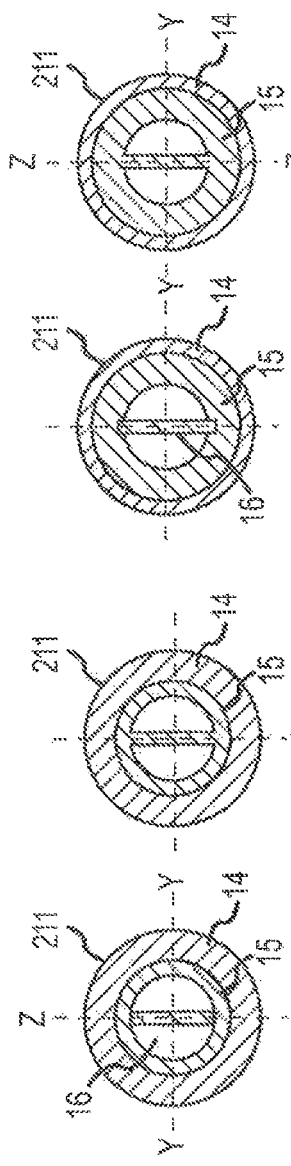
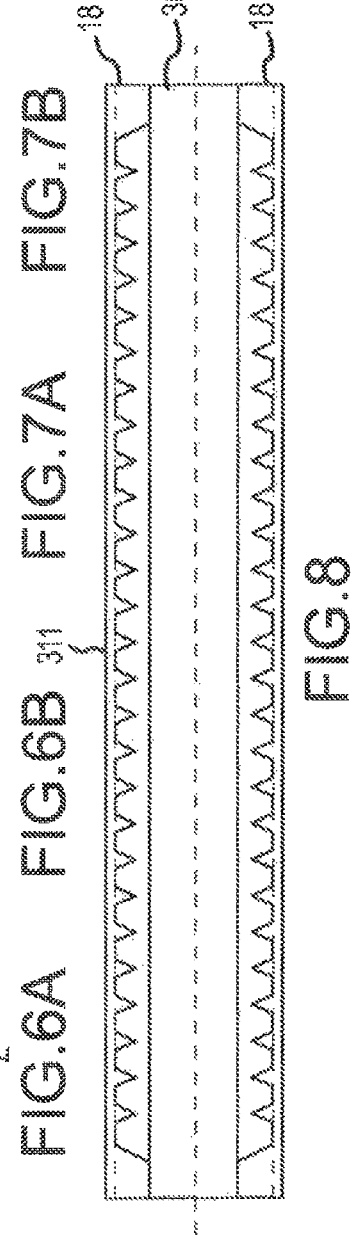
FIG. 5
FIG. 6A  FIG. 6B
FIG. 7A  FIG. 7B
FIG. 8

DEFLECTABLE CATHETER BODIES WITH CORRUGATED TUBULAR STRUCTURES

BACKGROUND

The instant disclosure relates to deflectable and steerable elongate devices, such as medical catheters. In particular, the instant disclosure relates to catheters having segments with anisotropic deflecting or bending stiffness that reduce or eliminate unintended out-of-plane movement of the catheter.

Deflectable and steerable elongate devices such as catheters are used for an ever-growing number of medical, industrial, and manufacturing procedures. For example, catheters are used for diagnostic, therapeutic, and ablative procedures. During these procedures, a catheter is typically inserted into a vessel near the surface of the body and is guided to a specific location within the body for examination, diagnosis, and treatment. A catheter typically carries one or more energy emitting elements (e.g., electrodes, hyperthermic ablation elements, cryogenic elements, etc.), which may be used for tissue ablation, diagnosis, or the like. Some catheters perform only passive or diagnostic functions such as sensing the electrical waveforms of a beating heart.

Catheters are often inserted into an artery or vein in the leg, neck, or arm of a patient and guided, sometimes with the aid of a guide wire or introducer, through the vessels until a distal end of the catheter reaches a desired location in the heart. Guidance of a catheter to a specific location in the body can be performed using feel, medical imaging (e.g., fluoroscopy), electrophysiological guidance (e.g., impedance-based and/or magnetic-based localization), computer generated maps/models, and/or various combinations of the above. In any case, it may be necessary to deflect or steer the distal end of the catheter to facilitate movement of the catheter through a body cavity (e.g., vessel) and/or to position the distal end of the catheter relative to an internal structure of interest.

In this regard, guidable catheters and/or introducers typically include a selectively deflectable segment near their distal tip. For instance, an ablation catheter may include a distal end portion (e.g., insertion portion) having an ablation electrode and a relatively soft and flexible distal deflectable segment that is disposed between the electrode and a relatively more rigid (e.g., metallic wire-braided.) catheter shaft that extends to a proximal actuator. Pull wires may extend from a pull mechanism in the proximal actuator and attach to a pull ring positioned between the deflectable segment and the electrode, Upon manipulation of the actuator, the pull wires can generate a pull force that imposes a bending moment on the flexible deflectable segment. This can lead to the deflection of the distal end of the catheter, which allows the distal end to be routed to and/or positioned relative to the desired internal locations.

One or more highly flexible polymer materials are typically used to construct a single or multi-segment deflectable body of the catheter. The catheter shaft proximally adjacent to the deflectable segment(s) typically consists of relatively rigid polymer materials. To improve the deflection planarity (i.e., in-plane deflection), prior catheters have incorporated various selectively deflectable segments or catheter bodies having anisotropic bending stiffness into deflectable segments or bodies of the catheters. Other catheters have used a "center strut" bonded to the deflecting portion to assist with maintaining catheter rigidity. See, e.g., U.S. patent application publication No. 2010/0063441, which is hereby incorporated by reference as though fully set forth herein.

Difficulties with the aforementioned catheters include failing to systematically and synergistically consider axial curvatures, deflection easiness, deflection in-planarity, and elastic recovery after deflection. Deflection planarity and ease of deflection are highly desirable properties or features for a deflectable catheter.

BRIEF SUMMARY

Among other things, various embodiments disclosed herein are directed to a family of deflectable or steerable and flexible devices such as medical catheters that facilitate movement of the distal tip of the device.

According to a first aspect, a guidable catheter is provided. The catheter includes a catheter body that has a proximal portion and a distal portion where the distal portion is adapted for insertion into a body cavity (e.g., internal tissue lumen, blood vessel, etc.). A deflectable segment is incorporated into the distal portion of the catheter body. The deflectable segment may be interconnected (e.g., axially) to the proximal portion of the catheter body by one or more pull wires. Upon actuation of such pull wires the distal deflectable segment may be deflected to move/sweep the distal catheter tip within a virtual plane called a sweeping plane.

The deflectable segment may be substantially tubular and may include a central lumen. Furthermore, the deflectable segment may have a first layer having a first corrugated surface and a second layer having a second corrugated surface. The first and second corrugated surface may be adjacent. The first corrugated surface may include a plurality of troughs and ridges, and the second corrugated surface may also include a second plurality of troughs and ridges. The first plurality of troughs and ridges may be complementary with the second plurality of troughs and ridges. In some embodiments, the first and second corrugated surfaces are bonded together.

The deflectable bodies may be axially comprised of two corrugate tubes which can be converted to intimately bonded and interlocked-in-place tubular structures after manufacture. The corrugation may comprise a plurality of peaks 40 and troughs 41, also referred to as radial ridges and troughs or valleys. The two corrugate tubes or layers for each deflectable body may be made of chemically compatible thermoplastic elastomer materials. In some embodiments, the corrugate tubes have different degrees of stiffness, flexibility or hardness. In addition, the corrugate tubes may have different melting or softening temperatures. The melting point of the first layer may differ from the melting point of the second layer by 20-30 degrees. In some embodiments, the first layer is Polyamide 12 and the second layer is a poly(ether block amide) copolymer. In at least one embodiment, the melting point of the first layer is greater than the melting point of the second layer. In at least one embodiment, the melting point of the first layer is less than the melting point of the second layer.

In at least one embodiment of the invention, the catheter has a tip electrode disposed at the distal end of the catheter body. The tip electrode has an internal lumen which is aligned with and in communication with the central lumen of the deflectable segment. The catheter may also have a deflection actuating structure that includes an annular ring disposed between the distal portion of the deflectable segment and the tip electrode and first and second pull wires extending from the proximal portion of the catheter body and interconnected to the annular ring. The catheter may have a stiffening element disposed along a portion of a length of the deflectable segment.

BRIEF DESCRIPTION OF THE DRAWINGS

FIG. 5 illustrates one example of a device having corrugated layers and a stiffening element.

FIG. 6A is a cross-sectional view taken along line 6-6 in FIG. 5. FIG. 6B is a cross-sectional view of another embodiment also taken along line 6-6 in FIG. 5.

FIG. 7A is a cross-sectional view taken along line 7-7 in FIG. 5. FIG. 7B is a cross-sectional view of another embodiment also taken along line 7-7 in FIG. 5.

FIG. 8 illustrates an example of a device having corrugated layers.

DETAILED DESCRIPTION

Figure 1:
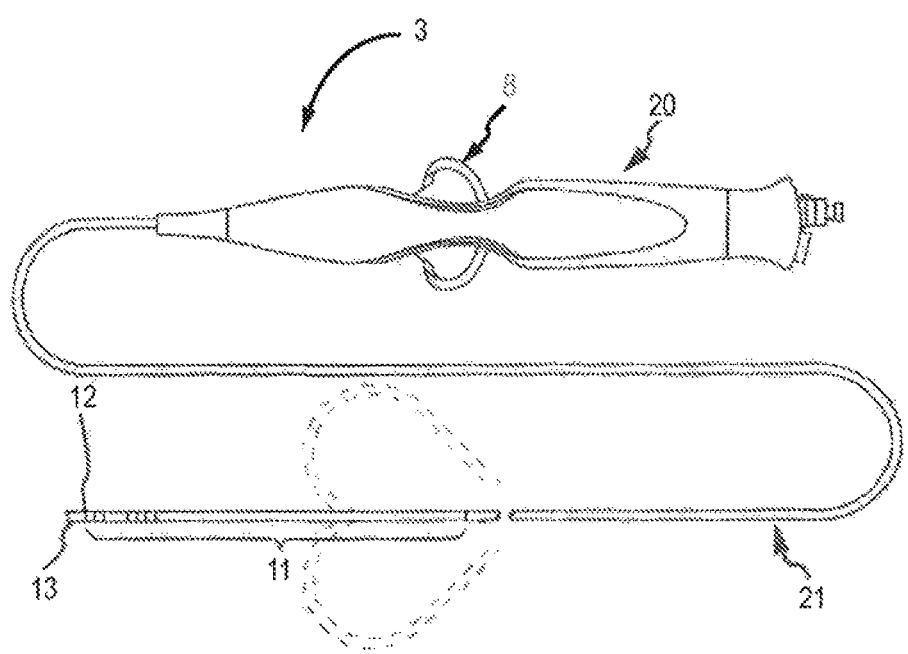
FIG. 1 illustrates an exemplary catheter.

Various embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a physician manipulating one end of an instrument used to treat a patient. The term "proximal" refers to the portion of the instrument closest to the physician and the term "distal" refers to the portion located furthest from the physician. Similarly, "more proximal" means closer to the physician whereas "more distal" means further form the physician. It will be further appreciated that for conciseness and clarity, spatial terms such as "vertical," "horizontal," "up," d "down" may be used herein with respect to the illustrated embodiments. However, surgical instruments may be used in many orientations and positions, and these terms are not intended to be limiting and absolute.

The present disclosure is generally directed towards a family of medical devices having deflectable segments including corrugated layers. Exemplary embodiments of such devices are depicted in the figures. As described further below, use of a catheter having a distal deflectable segment having anisotropic bending properties allows for improved catheter guidance and/or improved control for tissue access and tissue contact. As used herein, a "catheter" means an elongated structure that can be inserted into and/or through a body cavity, duct, and/or vessel. In at least one embodiment, a catheter may be hollow and/or define a lumen therethrough for passing another medical device, such as a guidewire or another catheter, for example. However, in various embodiments, a catheter may be closed at least at its distal end.

Referring now to the drawings wherein like reference numerals are used to identify identical or similar components in the various views, FIG. 1 generally illustrates a deflectable electrophysiology catheter 3 that comprises a tubular body or shaft 21 extending from a proximal handle 20. As used herein and commonly used in the art, the term "distal" is used generally to refer to components of the system, such as a tip electrode 13, located toward the insertion end of the of the catheter 3 (i.e., toward the heart or other target tissue when the catheter is in use). In contrast, the term "proximal" is used generally to refer to components or portions of the system that are located or generally orientated toward the non-insertion end of the catheter (i.e., away from or opposite the heart or other target tissue when the catheter is in use). Catheter 3 may be used in any number of diagnostic and therapeutic applications, such as the recording of electrograms in the heart, the performance of a cardiac ablation procedure, and other similar applications/procedures.

The proximal handle 20 includes an actuator 8 that is interconnected via one or more pull wires (not shown) to a distal deflectable segment 11 that is incorporated into the distal portion of the catheter 3. In some embodiments it may be beneficial to constrain movement of the catheter tip to a consistent and repeatable plane when actuated by a pull wire in order to facilitate deflection movement of the distal tip of a catheter or other medical device. That is, upon pulling a pull wire (e.g., actuation) to deflect the distal tip of the catheter, the catheter tip may deflect within a sweeping plane that is repeatable from actuation to actuation. However, in extant devices, the tip of the catheter is often able to move out of the desired sweeping plane. That is, deflection of the distal tip of extant devices may not be consistent between actuations. Therefore, in some embodiments it may be beneficial to provide a distal deflectable segment that constrains the movement of the distal tip of the catheter in a predictable and consistent manner as described further below.

As shown in FIG. 1, the distal tip of the exemplary catheter includes an ablation tip/electrode 13. Located proximally behind the electrode 13 is a pull ring 12 and the distal deflectable segment 11. The proximal end of the distal deflectable segment 11 is connected to the distal end of the catheter shaft 21. Additional details regarding such a catheter may be found in U.S. patent application Ser. No. 13/838,124, incorporated by reference as though fully set forth herein.

Figure 2:
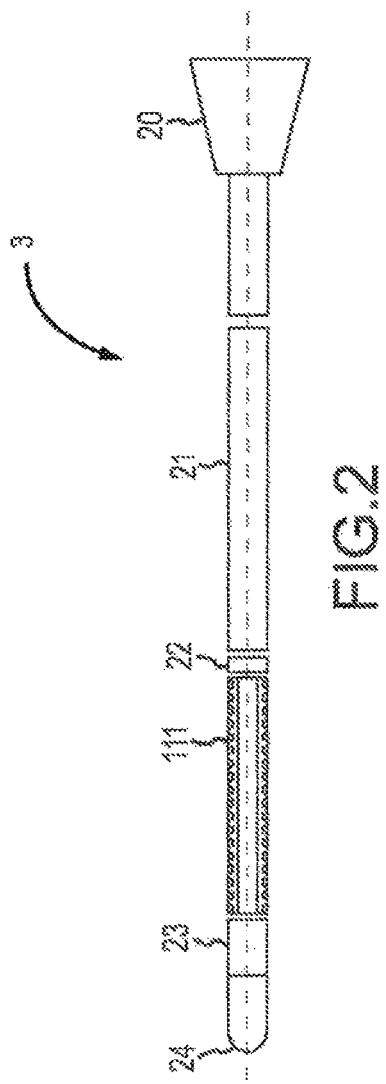
FIG. 2 is a diagrammatic representation of a catheter in a neutral or non-deflected state.
Figure 3:
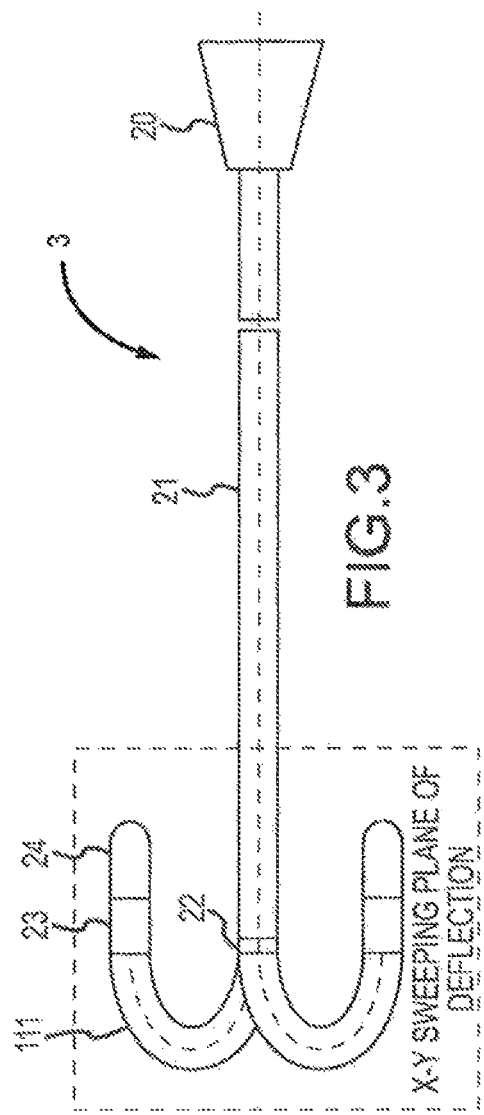
FIG. 3 is a diagrammatic representation of a catheter in a deflected state.

FIGS. 2 and 3 illustrate an enhanced view of the catheter 3. The catheter 3 includes a tubular body or shaft 21 extending from the proximal handle 20. Distal to the shaft 21 is a deflectable segment 111. Between the shaft 21, consisting of relatively rigid polymer(s), and the deflectable segment 111, containing a softer polymer, is a shaft transition region 22 largely comprised of a polymer with an intermediate material rigidity. Connecting the deflectable segment 111 and a distal tip 24 is a distal transition region 23. FIG. 3 illustrates the deflectable segment 111 deflecting in the X-Y sweeping plane of deflection.

Generally, the plane for deflection within which a deflectable segment has the greatest bending stiffness may define a reinforced plane of the segment. The plane for deflection within which the segment has the lowest bending stiffness may define a virtual, sweeping plane. The sweeping plane is typically perpendicular to the reinforced plane, and both planes pass through a reference, longitudinal axis (e.g., central X-axis in the neutral position) of the deflectable segment along its length.

Figure 4A:
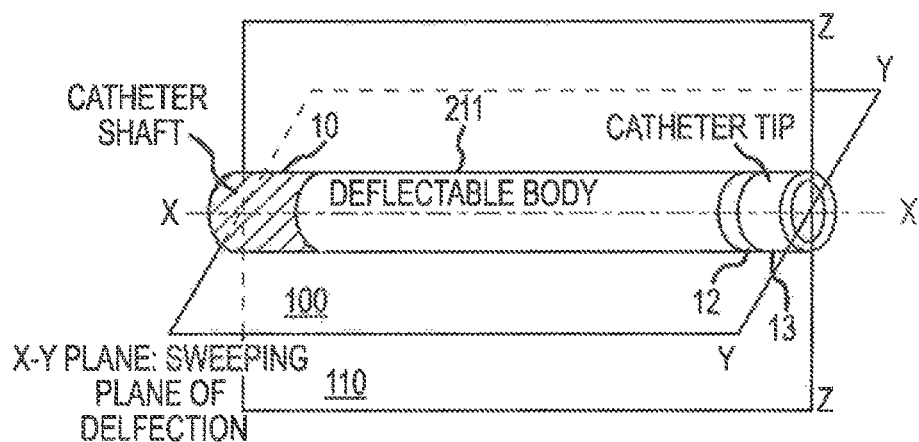
FIG. 4A illustrates a distal deflectable segment of an exemplary catheter in a neutral or non-deflected state.
Figure 4B:
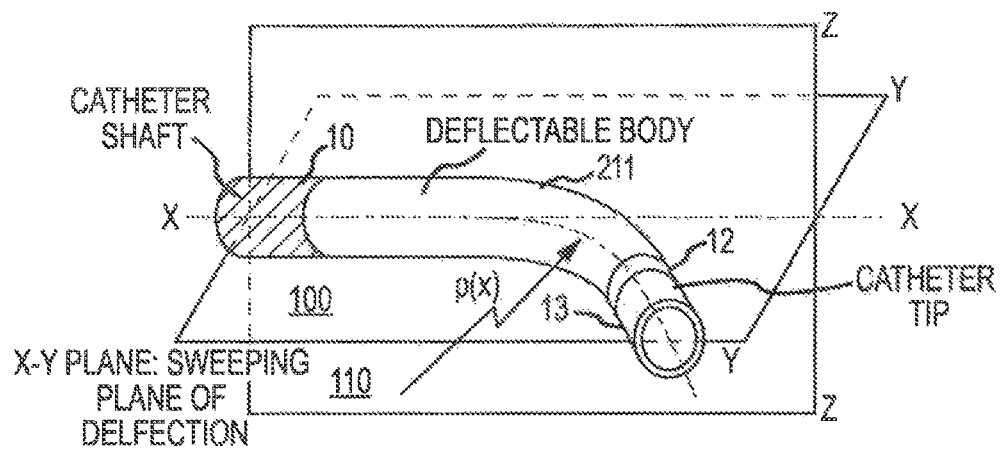
FIG. 4B illustrates a distal deflectable segment of an exemplary catheter in a deflected state.

FIGS. 4A and 4B illustrate an example of the distal deflectable segment according to the present teachings. As shown in FIG. 4A, in a neutral, non-deflected state, the distal deflectable segment 211 extends, as a substantially tubular structure, between the distal end of a catheter shaft 10 and a tip electrode 13. Generally, the catheter shaft 10 is more rigid than the distal deflectable segment 211. For instance, the catheter shaft 10 may be formed of a flexible resilient material covered by a wire-braiding that may extend to a proximal handle 20 (not shown in FIGS. 4A and 4B). Such construction is well understood and need not be further described herein.

In one exemplary embodiment, the shaft 10 is fabricated with a flexible resilient material. The shaft 10 can be fabricated of materials suitable for use in humans, such as biocompatible polymers. Suitable polymers include those well known in the art, such as numerous thermoplastics including, but not limited to, fluoropolymers, polyolefins, polyesters, polyamides, polycarbonate, polyurethanes, polyimides, polysulfones, polyketones, liquid crystal polymers and the like. Various thermoplastic elastomer (TPE) materials can also be selected, including, but not limited to, thermoplastic polyurethanes, polyamide-based TPE's, polyester-based TPE's, thermoplastic polyolefins, and styrenic TPE's.

Located proximally behind the electrode 13 is a pull ring 12. In order to deflect the deflectable segment 211, pull wires (not shown) may extend from an actuator mechanism in a catheter handle (see, e.g., handle 20 shown in FIG. 1) and attach to pull ring 12 located in the proximal vicinity of tip electrode 13.

As illustrated in FIG. 4B, the distal tip (e.g., tip electrode 13) is caused to move within a bending or sweeping plane 100 (e.g., the X-Y plane). Such constraint to the desired sweeping plane may provide consistent and predictable displacement between deflections of the catheter.

Previous deflectable segments have permitted some out-of-plane movement, which may be undesirable. To overcome these problems and minimize out-of-plane deflection, the distal deflectable segment 211 disclosed herein has anisotropic bending stiffness to facilitate the isolation of deflections of the segment 211 to a desired plane (e.g., the sweeping plane 100). As such, in its neutral position, the deflectable segment 211 has minimal bending moment of section bending stiffness about the Z-Z axis, which is perpendicular to the designated sweeping plane of deflection, namely the X-Y plane.

As shown in FIG. 5, the deflectable segment 211 comprises interlocking, corrugated tubular structures that provide smooth curvatures of desirable configurations, deflection planarity and manipulation easiness. The corrugated structures for the segment 211 also lead to decreased kinking tendency and allow for high torque transfer from the shaft 10 to the tip electrode 13.

FIG. 5 illustrates a delectable segment 211 that includes two corrugated layers, 14 and 15. The deflectable segment 211 includes a first corrugated inner layer 15 and a second corrugated outer layer 14. Layers 14 and 15 can be made of chemically compatible thermoplastic elastomer materials. Layers 14 and 15 have different stiffness (or flexibility or hardness) and may further have different melting (or softening) temperatures. Thermoplastic elastomer materials can be selected from commercially available poly(ether-block-amide) copolymers (such as Pebax® and Vestamid® E), the thermoplastic polyurethane elastomers (such as Pellethane®, Tecoflex®, Tecoplast®, Tecothane®, Carbothane®, Elasthane®, Bionate®, Biospan®, Pursil®, and Carbosil®), polyester-based thermoplastic elastomers such as Hytrel® and Arnitel®), polyamides (PA11, PA12, PA612, etc.), polyesters such as PET and PBT, poly(bisphenol A carbonate), and the like. In some embodiments, the thermoplastic elastomer material is selected from PA11, PA12, and PA612.

Figure 11:
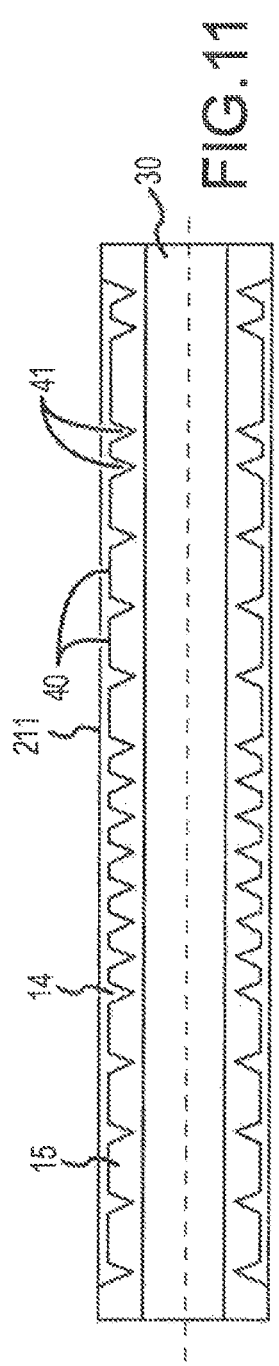

To manufacture the deflectable segment 211, the inner layer 15, which may have either consistent and uniform corrugation patterns or axially varying patterns (for example, as shown in FIG. 11), can be prepared from a polymer having a higher melting (or softening) temperature than the outer layer 14 using injection molding, compression molding, or 3D printing. The inner layer 15 will form a corrugated tubular structure having a central lumen 30. The second outer layer 14 can be pre-extruded into tubing from other polymer having a lower melting (or softening) temperature than the inner layer 15, and then applied onto the pre-molded inner layer 15. Upon thermal fusion or reflow processes, the outer layer 14 will fill into the valleys of the corrugated inner layer 15, and adhere onto the corrugated surfaces of the inner layer 15. In the end, the layers 14 and 15 will be integrated into an inseparable deflectable segment. The corrugations of layer 14 will be complementary to the corrugations of layer 15, but it should be understood that the term "complementary" does not mean that there are no gaps between the corrugations of layers 14 and 15. Indeed, it is contemplated that interstitial spaces will remain between layers 14 and 15.

To facilitate bonding of layers 14 and 15, in some embodiments, a shrink tubing may be applied onto the second outer layer 14, and a metallic rod may be inserted into the lumen 30 of the inner layer 15. Upon uniform heating onto the shrink tube, the outer layer 14 melts and fills into the corrugations of the inner layer 15 under the inwards shrink pressure arising from the shrink tube, while the metallic rod preserves the integrity of central lumen 30. During the processes, the pre-molded inner layer 15 remains in its solid state because of its higher melting point.

To achieve suitable thermal fusion between the pre-molded inner layer 15 and the pre-extruded outer layer 14, the melting (or softening) temperature for the inner layer 15 should be at least 10° C. higher than that of the outer layer 14. In sonic embodiments, the melting (or softening) temperature for the inner layer is about 20-30° C. greater than that of the outer layer 14. For example, PA12 having a melting temperature ranging from 175 to 180° C. can be used for the inner layer 15, while a poly(ether block amide) copolymer (PEBA), such as Pebax®) 5533 SA 01 (having the melting temperature of about 160° C.) or Pebax® 4033 SA 01 (having the melting temperature of about 147° C.), or Pebax® 3533 SA 01 (having the melting temperature of about 144° C.) can be used as the outer layer 14.

In another example, the inner layer 15 can be made of Pebax® 7233 SA 01 and the outer layer 14 can be made of Pebax® 4033 SA 01 or Pebax® 3533 SA 01 or Pebax® 2533 SA 01.

In another example, the inner layer 15 is made of PA11, and the outer layer 14 is made of a polytetramethylene glycol based polyurethane elastomer such as Pellethane® 2363-90AE or Pellethane® 2363-80AE.

In another embodiment, the polymers of inner layer 15 and outer layer 14 can be selected to have distinctly different hardness but similar softening temperatures for melt processing. In such embodiments, a highly flexible elastomeric adhesive layer, such as proper urethane adhesives and silicone adhesives, can be introduced between the inner layer 15 and outer layer 14 to fill in any gaps between the complementary peaks (or ridges) and troughs (or valleys) of layers 15 and 14. The curing temperature for the adhesives should not soften the body materials.

As shown in FIG. 5, the deflectable segment 211 can have a stiffening element 16 such as those disclosed in U.S. Pat. No. 7,985,215, which is hereby incorporated in its entirety by reference. The stiffening element 16 has a Young's modulus greater than the Young's modulus of the surrounding material of the deflectable segment 211.

The stiffening element 16 may extend over the entirety of the length of the deflectable segment 211 and/or multiple stiffening elements 16 may be disposed in, for example, series and/or parallel. In one arrangement, stiffening elements 16 have a Young's modulus that is greater than the Young's modulus of the material forming the deflectable segment 211. In such an arrangement, stiffening elements 16 may be formed of for example, relatively rigid polymeric material and/or metallic material. In any arrangement, the cross section of a stiffening element 16 may have an area moment of inertia about a first centroidal axis that is greater than an area moment of inertia about a second centroidal axis. In this regard, the stiffening element 16 may permit bending or deflection in a plane in parallel with the first centroidal axis, while significantly restricting bending in another plane. Accordingly, such a stiffening element 16 may be disposed in the vicinity of a reinforced plane of a distal deflectable segment 211 to prevent out-of-plane movement while permitting in-plane movement (e.g., sweeping plane movement).

FIGS. 6A, 6B, 7A, and 7B show various cross-sections of deflectable segment 211, depicted in FIG. 5, including stiffening elements 16. In FIGS. 6A and 7A, the stiffening element 16 is a separate, rigid and thin center element that can be inserted and integrated into the inner layer 15 as disclosed in U.S. Pat. No. 7,985,215. The stiffening element 16 helps improve the deflection planarity within the sweeping plane, i.e., XY plane. The stiffening element 16 as shown in FIGS. 6A and 7A can be made of a rigid thermoplastic having a higher hardness than either layer 15 or layer 14. In some embodiments, the stiffening element 16 is a thin sheet metal. In an alternative embodiment depicted in FIGS. 6B and 7B, the stiffening element 16 is part of the pre-molded inner layer 15.

Thus, stiffening element 16 can be made of metals or metallic alloys commonly used for reinforcing catheter shafts, including steels, stainless steels, NiTi alloys, tungsten, and others. Also, those stiffening materials can be engineering polymers such as polycarbonates, nylons, polyesters, polyurethanes, nylon-based copolymers, polystyrenes, poly(methyl methacrylate), polysulfones, liquid crystalline polymers, and the like.

The stiffening element 16 is placed near a neutral in-plane bending axis, i.e., Z-axis. Therefore, the stiffening element 16 has minimal contribution to the in-plane bending stiffness about the neutral in-plane bending axis, i.e., Z-axis. However, due to the high Young's modulus of the stiffening element 16, the stiffening element 16 increases the out-of-plane bending stiffness about the neutral out-of-plane bending axes, i.e., X-axis and Y-axis.

FIG. 8 shows a deflectable segment 311 having at least one metal braid assembly 18 axially extending into part or all of the deflectable segment 311. The metal braid assembly 18 may be a braided wire mesh. The metal braid assembly 18 may be formed of stainless steel wire. The metal braid assembly may be formed separately on a disposable core and slipped about inner layer 15 of the deflectable segment. Those of skill in the art will be familiar with the use of braid assembly 18 in catheter construction, and thus it need not be described further herein.

Figure 9:
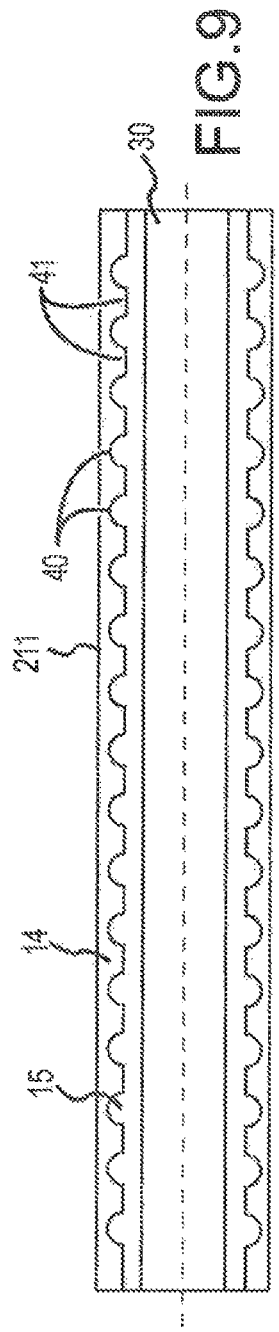
FIGS. 9-11 illustrate examples of different patterns of corrugation that can be used in a deflectable segment of an exemplary catheter.
Figure 10:
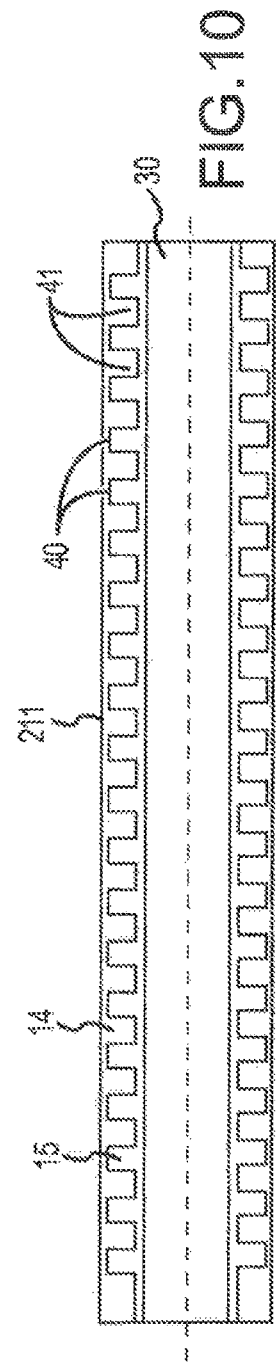

FIGS. 9-11 illustrate a variety of possible contours for the corrugated, inner layer 15 of the deflectable body 211. The corrugation can take various regular or irregular geometries such as semi-circular, rectangular, triangular, trapezoidal, sinusoidal, wave-like, and the like. FIG. 9 represents a semi-circle variation, FIG. 10 represents a rectangular variation, and FIG. 11 represents an altered axial repeating pattern. As shown, the corrugation profile can remain uniform throughout deflectable segment 211 or may vary axially. If it varies, it may be a repeating pattern or a non-repetitive design.

Although several embodiments of this disclosure have been described above with a certain degree of particularity, those skilled in the art could make numerous alterations to the disclosed embodiments without departing from the scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the embodiments of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A catheter, comprising:
a catheter body having a proximal portion and a distal portion; and
a deflectable segment in the distal portion, wherein the deflectable segment includes a central lumen comprising an axis, a proximal portion, and a distal portion, and wherein the deflectable segment comprises:
a first layer comprising a first corrugated surface, wherein the first layer extends circumferentially around the central lumen of the deflectable segment, and wherein the first corrugated surface extends longitudinally along the axis of the central lumen of the deflectable segment, and further wherein the first layer comprises a first biocompatible polymer; and
a second layer comprising a second corrugated surface, wherein the second layer extends circumferentially around the first layer, and wherein the second corrugated surface extends longitudinally along the axis of the central lumen of the deflectable segment, and further wherein the second layer comprises a second biocompatible polymer,
wherein the first and second corrugated surfaces are adjacent, and
wherein the first corrugated surface includes a first plurality of annular troughs and annular ridges that alternate along a length of the first layer and the second corrugated surface includes a second plurality of annular troughs and annular ridges that alternate along a length of the second layer, wherein the first plurality of annular troughs and annular ridges are complementary with the second plurality of annular troughs and annular ridges, and wherein the first corrugated surface extends circumferentially around the entire central lumen, and wherein the second corrugated surface extends circumferentially around the entire first corrugated surface.

2. The catheter of claim 1, wherein the deflectable segment is substantially tubular.

3. The catheter of claim 1, wherein the first and second corrugated surfaces are bonded together.

4. The catheter of claim 1, wherein the first biocompatible polymer and second biocompatible polymer comprise chemically compatible thermoplastic elastomer materials.

5. The catheter of claim 4, wherein the first layer and second layer have different melting points.

6. The catheter of claim 5, wherein the melting point of the first layer differs from the melting point of the second layer by 20-30 degrees.

7. The catheter of claim 5, wherein the first layer is comprised of polyamide 12 and wherein the second layer is comprised of a poly(ether block amide) copolymer.

8. The catheter of claim 7, wherein the melting point of the first layer differs from the melting point of the second layer by 20-30 degrees.

9. The catheter of claim 7, wherein the durometer of the first layer is different from the durometer of the second layer.

10. The catheter of claim 7, wherein the melting point of the first layer is greater than the melting point of the second layer.

11. The catheter of claim 7, wherein the melting point of the first layer is less than the melting point of the second layer.

12. A catheter, comprising:
a catheter body having a proximal portion and a distal portion;
a deflectable segment in the distal portion, wherein the deflectable segment includes a central lumen comprising an axis, a proximal portion, and a distal portion, and wherein the deflectable segment comprises:
a first layer comprising a first corrugated surface, wherein the first layer extends circumferentially around the central lumen of the deflectable segment, and wherein the first corrugated surface extends longitudinally along the axis of the central lumen of the deflectable segment, and further wherein the first layer comprises a biocompatible polymer; and
a second layer comprising a second corrugated surface, wherein the second layer extends circumferentially around the first layer, and wherein the second corrugated surface extends longitudinally along the axis of the central lumen of the deflectable segment, and further wherein the second layer comprises a biocompatible polymer, and
wherein the first and second corrugated surfaces are adjacent, wherein the first corrugated surface includes a first plurality of annular troughs and annular ridges that alternate along a length of the first layer and the second corrugated surface includes a second plurality of annular troughs and annular ridges that alternate along a length of the second layer, wherein the first plurality of annular troughs and annular ridges are complementary with the second plurality of annular troughs and annular ridges, and wherein the first corrugated surface extends circumferentially around the entire central lumen, and wherein the second corrugated surface extends circumferentially around the entire first corrugated surface; and
a tip electrode, disposed at a distal end of the catheter body; and
a deflection actuating structure including:
an annular ring disposed between the distal portion of the deflectable segment and the tip electrode; and
first and second pull wires extending from the proximal portion of the catheter body and interconnected to the annular ring.

13. The catheter of claim 12, wherein the catheter further comprises:
a stiffening element disposed along a portion of a length of the deflectable segment.

14. A catheter having a proximal portion and a distal portion, the catheter comprising:
a distal deflectable segment, wherein the deflectable segment includes an inner lumen comprising an axis, the deflectable segment comprising a proximal end and a distal end, and wherein the deflectable segment comprises:
a first layer having a first corrugated surface, wherein the first layer extends circumferentially around the inner lumen of the deflectable segment, and wherein the first corrugated surface extends longitudinally along the axis of the inner lumen of the deflectable segment, and further wherein the first layer comprises a first biocompatible polymer; and a second layer having a second corrugated surface, wherein the second layer extends circumferentially around the first layer, and wherein the second corrugated surface extends longitudinally along the axis of the inner lumen of the deflectable segment, and further wherein the second layer comprises a second biocompatible polymer, and wherein the first and second corrugated surfaces are adjacent, and wherein the first corrugated surface includes a first plurality of annular troughs and annular ridges alternating along a length of the first layer and the second corrugated surface includes a second plurality of annular troughs and annular ridges alternating along a length of the second layer, wherein the first plurality of annular troughs and annular ridges are complementary with the second plurality of annular troughs and annular ridges, and wherein the first corrugated surface extends circumferentially around the entire central lumen, and wherein the second corrugated surface extends circumferentially around the entire first corrugated surface; and a tip electrode including an internal lumen, wherein the tip electrode is disposed at the distal end of the deflectable segment and wherein the internal lumen of the tip electrode is aligned with and in communication with the inner lumen of the deflectable segment.

15. The catheter of claim 14, wherein the plurality of troughs and ridges are selected from a semi-circle variation, a rectangular variation, and an altered axial repeating pattern.

16. The catheter of claim 14, wherein the first biocompatible polymer and second biocompatible polymer comprise chemically compatible thermoplastic elastomer materials.

17. The catheter of claim 16, wherein the first layer and second layer have different melting points.

18. The catheter of claim 17, wherein the melting point of the first layer is about 20-30 degrees greater or less than the melting point of the second layer.

19. The catheter of claim 17, wherein the first layer is comprised of polyamide 12 and wherein the second layer is comprised of a poly(ether block amide) copolymer.

20. A catheter, comprising:

a catheter body having a proximal portion and a distal portion; and a deflectable segment in the distal portion, wherein the deflectable segment includes a central lumen comprising an axis, a proximal portion, and a distal portion, and wherein the deflectable segment comprises:

a first layer comprising a first corrugated surface, wherein the first layer extends circumferentially around the entire central lumen of the deflectable segment, and wherein the first corrugated surface includes a first plurality of annular troughs and annular ridges alternating along a length of the first layer, and further wherein the first layer comprises a first biocompatible polymer; and a second layer comprising a second corrugated surface, wherein the second layer extends circumferentially around the entire first layer, and wherein the second corrugated surface includes a plurality of annular troughs and annular ridges alternating along a length of the second layer, and further wherein the second layer comprises a second biocompatible polymer, wherein the first and second corrugated surfaces are adjacent, and wherein the first plurality of annular troughs and annular ridges are complementary with the second plurality of annular troughs and annular ridges; and wherein the deflectable segment comprises an outer surface, wherein the outer surface is smooth, and wherein the diameter of the outer surface is constant.

* * * * *